United States Patent [19]

Bennett

[11] 4,285,944
[45] * Aug. 25, 1981

[54] PYRANO[4,3-e]-AS-TRIAZINES AND CORRESPONDING 4-OXIDES

[75] Inventor: Gregory B. Bennett, Mendham, NJ

[73] Assignee: Sandoz, Inc., E. Hanover, N.J.

[*] Notice: The portion of the term of this patent subsequent to Oct. 14, 1997, has been disclaimed.

[21] Appl. No.: 139,109

[22] Filed: Apr. 10, 1980

Related U.S. Application Data

[63] Continuation of Ser. No. 65,279, Aug. 9, 1979, abandoned, which is a continuation of Ser. No. 957,189, Nov. 2, 1978, abandoned.

[51] Int. Cl.³ .................. C07D 491/08; A61K 31/53
[52] U.S. Cl. .................................. 424/249; 544/184
[58] Field of Search ...................... 544/184; 424/249

[56] References Cited

U.S. PATENT DOCUMENTS 4,228,280 10/1980 Bennett ............................ 544/184

Primary Examiner—John M. Ford
Attorney, Agent, or Firm—Gerald D. Sharkin; Robert S. Honor; Timothy G. Rothwell

[57] ABSTRACT

This disclosure describes novel compounds of the formula

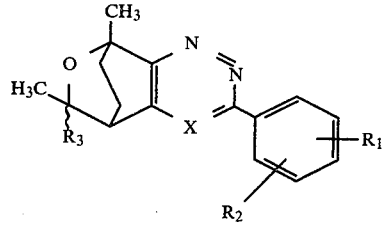

wherein
$R_1$ and $R_2$ each independently represent hydrogen, halo having an atomic weight of about 19 to 36, lower alkyl, straight chain lower alkoxy, amino, nitro or trifluoromethyl, and
$R_3$ represents hydrogen or lower alkyl, and
X represents

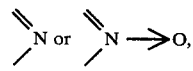

which are useful as sleep inducers.

18 Claims, No Drawings

PYRANO[4,3-e]-AS-TRIAZINES AND CORRESPONDING 4-OXIDES

This is a continuation, of application Ser. No. 65,279, filed Aug. 9, 1979, now abandoned, which in turn is a continuation, of application Ser. No. 957,189, filed Nov. 2, 1978, now abandoned.

This invention relates to organic compounds and more particularly to 5,8-ethano-pyrano[4,3-e]-as-triazines and corresponding 4-oxides, pharmaceutically acceptable salts, as well as the pharmaceutical use of such compounds, particularly as sleep inducers.

The compounds of this invention may be represented by the following structural formula:

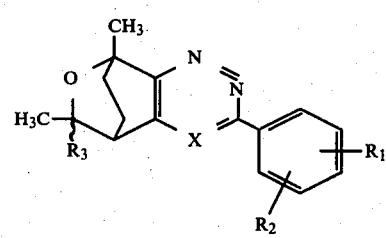

(I)

wherein

R$_1$ and R$_2$ each independently represent hydrogen, halogen having an atomic weight of about 19 to 36, lower alkyl, i.e., alkyl having 1 to 4 carbon atoms, e.g., methyl, ethyl, isopropyl and the like, straight chain lower alkoxy, i.e., alkoxy having 1 to 4 carbon atoms, e.g., methoxy, ethoxy and the like, amino, nitro or trifluoromethyl, and R$_3$ represents hydrogen or lower alkyl, having 2 to 4 carbon atoms, i.e., ethyl, propyl and the like, and X represents

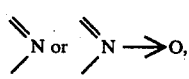

provided that
(i) when one of R$_1$ and R$_2$ represents nitro, the other is other than nitro or trifluoromethyl;
(ii) when R$_1$ and R$_2$ represent trifluoromethyl, they are on other than adjacent carbon atoms; an
(iii) when R$_1$ and R$_2$ represent t-butyl, they are on other than adjacent carbon atoms; and
(iv) when one of R$_1$ and R$_2$ is trifluoromethyl and the other is t-butyl, they are on other than adjacent carbon atoms.

The compounds of formula (I) in which X represents

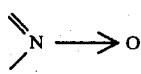

may be prepared according to the following reaction scheme:

where
R$_4$ represents lower alkyl having 1 to 2 carbon atoms, i.e., methyl or ethyl, and
R$_1$, R$_2$, R$_3$ and the provisos are as defined above.

The compounds of formula (Ia) are prepared by treating a compound of the formula (II) with a compound of the formula (III) in the presence of an inert atmosphere, e.g., nitrogen, helium or argon and in the presence of an inert organic solvent. Although the particular solvent employed is not critical, the preferred solvents include the aromatic hydrocarbons such as benzene, toluene and the like, the lower alkanols such as methanol, ethanol and the like, or an excess of the ortho ester of formula (III), the latter being especially preferred. The temperature of the reaction is not critical, but it is preferred that the reaction be run from about 70° to 200° C., preferably from about 130° to 150° C. The reaction is run from about 12 to 36 hours, preferably from about 15 to 20 hours. The product is recovered using conventional techniques, e.g., filtration.

The compounds of formula (I) in which X represents

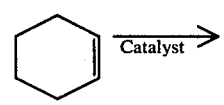

may be prepared according to the following reaction scheme:

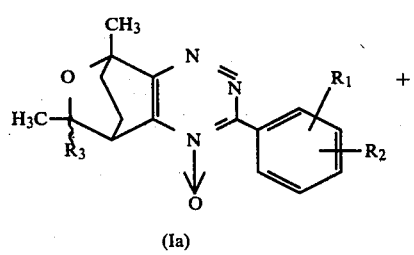

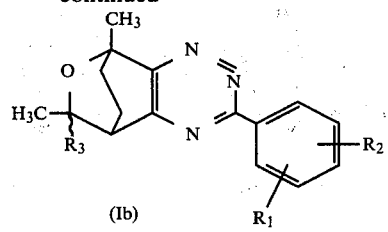

(Ib)

where $R_1$, $R_2$, $R_3$ and the proviso are as defined above.

The compounds of formula (Ib) are prepared by treating a compound of the formula (Ia) with cyclohexene (IV) in an inert atmosphere, e.g., nitrogen, helium, or argon, preferably nitrogen, and in the presence of a noble metal catalyst such as palladium, platinum, rhodium and the like, preferably palladium, optionally near or on a support such as charcoal, in an inert organic solvent. Although the particular solvent used is not critical, it is preferred that the reaction be carried out in the presence of the lower alkanols, e.g., methanol, ethanol, and the like, preferably ethanol. Temperature of the reaction is not critical but it is preferred that the reaction be carried out between 20° to 200° C., preferably from about 70° to 110° C. The reaction is run from about 5 to 72 hours, preferably from about 15 to 30 hours. The product is recovered using conventional techniques, e.g., crystallization.

The compounds of formula (II) may be prepared according to the following reaction scheme:

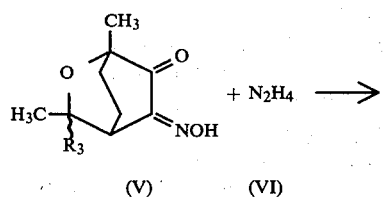

(V)  (VI)

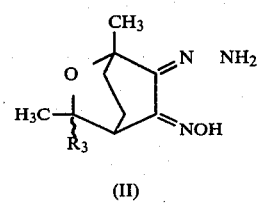

(II)

where $R_3$ is as defined above.

The compounds of formula (II) are prepared by treating a compound of the formula (V) with hydrazine (VI) in an inert atmosphere, e.g., nitrogen, helium or argon, preferably nitrogen in the presence of an inert organic solvent. Although the particular solvent employed is not critical, it is preferred that the reaction be carried out in the presence of the lower alkanols, e.g., methanol, ethanol and the like, preferably ethanol. The temperature of the reaction is not critical, but it is preferred that the reaction be carried out between 0° to 150° C., preferably from about 75° to 85° C. The reaction is run from about 1 to 18 hours, preferably from about 2 to 8 hours. The product is recovered using conventional techniques, e.g., crystallization.

The compounds of formula (V) are prepared in accordance with the following reaction scheme:

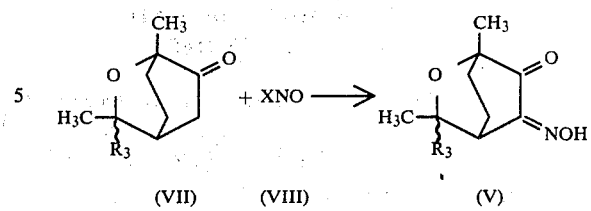

(VII)  (VIII)  (V)

wherein

X represents chloro or lower alkoxy, i.e., alkoxy having 1 to 5 carbon atoms, e.g., methoxy, ethoxy and the like, and $R_3$ is as defined above.

The compounds of formula (V) are prepared by nitrosating a compound of the formula (VII) with a compound of the formula (VIII) in the presence of an inert atmosphere e.g., nitrogen, helium or argon in the presence of an acid catalyst and inert organic solvent. Although the particular acid catalyst employed is not critical, it is preferred that the reaction be carried out in the presence of hydrogen chloride or boron trifluoride etherate, preferably hydrogen chloride. The particular solvent employed also is not critical, however, it is preferred that the reaction be carried out in the presence of an ether such as diethylether, tetrahydrofuran, dioxane and the like, or a halogenated hydrocarbon such as methylene chloride, chloroform and the like, preferably diethylether. The temperature of the reaction is not critical but it is preferred that the reaction be run from about −70° C. to 40° C., more preferably from about −50° C. to 0° C. The reaction is run from about 12 to 36 hours, preferably from about 23 to 26 hours. The product is recovered using conventional techniques, e.g., crystallization.

The compounds of formula (VII) are prepared in accordance with the following reaction scheme:

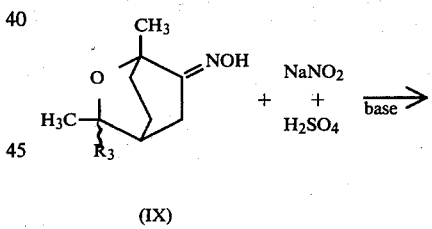

(IX)

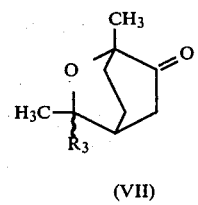

(VII)

wherein $R_3$ is as defined above.

The compounds of formula (VII) are prepared by reacting a compound of the formula (IX) with sodium nitrite and sulfuric acid in the presence of an inert organic solvent. Although the particular solvent employed is not critical, it is preferred that the reaction be run in a biphasic solvent system composed of water and an organic solvent such as an ether, e.g., tetrahydrofuran, diethylether, dioxane, and the like, preferably diethylether. The temperature of the reaction is not critical, but it is preferred that the reaction be run from 0° to 60° C., preferably from about 0° to 30° C. The reaction is run from about 1 to 8 hours, preferably from about 2 to 5 hours. While the particular base required for the second step is not critical, the preferred bases include the inorganic bases such as the alkali metal hydroxides, e.g., potassium hydroxide, sodium hydroxide and the like, or ammonium hydroxide, the latter being especially preferred. The product is recovered using conventional techniques, e.g., steam distillation and recrystallization.

The compounds of formula (IX) are prepared according to the following reaction scheme:

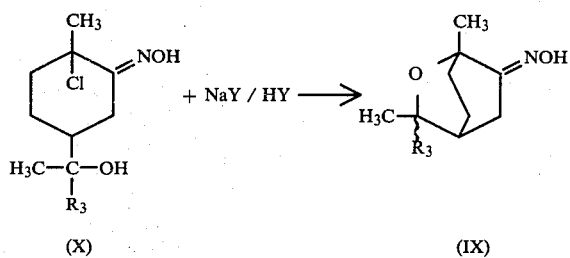

wherein
Y represents acetate or trifluoroacetate, and
R₃ is as defined above.

The compounds of formula (IX) are prepared by dehydrohalogenating a compound of the formula (X) with NaY, i.e., sodium acetate or sodium trifluoroacetate, preferably sodium acetate, in the presence of a solvent system HY, e.g., acetic acid or trifluoroacetic acid, preferably acetic acid. The temperature of the reaction is not critical, but it is preferred that the reaction be run from 30° to 120° C., preferably from about 90° to 110° C. The reaction is run from about 0.1 to 8 hours, preferably from about 0.5 to 3 hours. The product is recovered using conventional techniques, e.g., extraction and crystallization.

The compounds of formula (X) are prepared in accordance with the following reaction scheme:

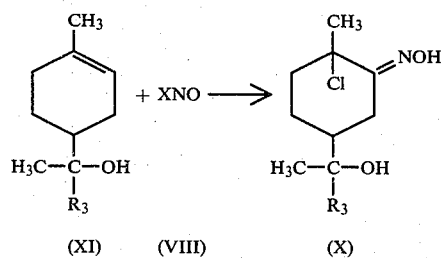

where X and R₃ are as defined above.

The compounds of formula (X) are prepared by nitrosating a compound of the formula (XI) with a compound of the formula (VIII) in the presence of an inert atmosphere, e.g., nitrogen, helium or argon in the presence of an acid catalyst and inert organic solvent. Although the particular acid catalyst employed is not critical, it is preferred that the reaction be carried out in the presence of hydrogen chloride gas or concentrated hydrochloric acid, the latter being especially preferred. The particular solvent employed also is not critical, however, it is preferred that the reaction be carried out in the presence of an ether such as diethylether, tetrahydrofuran, dioxane and the like, or a halogenated hydrocarbon such as methylene chloride, chloroform and the like, or acetic acid, preferably acetic acid. The temperature of the reaction is not critical but it is preferred that the reaction be run from about −70° C. to 40° C., more preferably from about −30° C. to 10° C. The reaction is run from about 1 to 24 hours, preferably from about 2 to 5 hours. The product is recovered by conventional techniques, e.g., extraction, filtration, followed by evaporation.

Certain of the compounds of formulae (III), (IV), (VI), (VIII), (X) and (XI) are known and may be prepared by methods described in the literature. Those compounds of formulae (III), (IV), (VI), (VIII), (X) and (XI) not specifically disclosed may be prepared by analogous methods from known starting materials.

It will be understood that the compounds of (I) may exist in the form of diastereomeric mixtures, and each of the diastereomers can exist as optically active isomers such as the (+)3-(m-trifluoromethylphenyl)-5,8-dihydro-6,8-dimethyl-5,8-ethano-6H-pyrano[4,3-e]as-triazine-4-oxide or the (−)3-(m-trifluoromethylphenyl)-5,8-dihydro-6,8-dimethyl-5,8-ethano-6H-pyrano[4,3-e]as-triazine-4-oxide, which can be separated and recovered by conventional techniques, and such isomeric forms are included within the scope of this invention.

The compounds of formula (I) are useful because they possess pharmacological activity in animals as sleep inducers as indicated (1) by the hexobarbital reinduction method of Winter, J. Pharmacol. and Exp. Therap., 94, 7–11, 1948; and (2) by their ability to produce docility in behavior tests in mice given 2.5 to 200 mg/kg of animal body weight, i.p. of the test compound according to the 30-word adjective check sheet, system basically as described by Irwin S. (Gordon Research Conference, Medicinal Chemistry, 1959) and Chen (Symposium on Sedative and Hypnotic Drugs, Williams and Wilkins, 1954).

The sleep inducing effective dosage of the compounds of formula (I) will vary depending on the particular compound employed. However, in general, satisfactory results are obtained when the compounds are administered orally at a daily dosage of from about 0.05 milligrams to about 50 milligrams per kilogram of animal body weight, typically given in a single dose at bedtime. For most large mammals, the total daily dosage is from about 0.5 to about 500 milligrams, preferably at bedtime and dosage forms suitable for internal administration comprise from about 0.125 to about 250 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For the use mentioned above, the compound may be administered orally in such forms as tablets, capsules, elixirs, suspensions and the like, or parenterally in the form of injectable solutions or suspensions. The dosage will vary depending upon the mode of administration utilized and the compound employed.

The compounds of formula (I) may be similarly administered in the form of their non-toxic pharmaceutically acceptable salts. Such salts possess the same order of activity as the free base and are readily prepared by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers in divided doses two to four times per day.

| Ingredients | Weight (mg.) Tablet | Capsule |
| --- | --- | --- |
| 3-(m-trifluoromethylphenyl)-5,8-dihydro-6,8-dimethyl-5,8-ethano-6H-pyrano[4,3-e]as-triazine-4-oxide | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

1,3-Dimethyl-2-oxabicyclo[2,2,2]octan-6-one oxime

To a mixture of 21.0 g. (0.133 mole) of 4-(1-hydroxyethyl)-1-methyl-cyclohexene, 23 mg. glacial acetic acid and 26 ml. n-butylnitrite at 0° C. there is added dropwise a solution of 5 ml. concentrated hydrochloric acid and 5 ml. glacial acetic acid. After two additional hours while maintaining the temperature at 0° C., 500 ml. water is added and the solution is extracted with diethyl ether. These ether extracts are washed with water and brine and dried over magnesium sulfate. The magnesium sulfate is removed by filtration and the solution evaporated to give 2-chloro-5-(1-hydroxyethyl)-2-methyl-cyclohexanone oxime. To this compound is added 12.0 g. anhydrous sodium acetate and 50 ml. glacial acetic acid. This mixture is heated at 100° for one hour and poured into 250 ml. water. After sitting for several hours, the aqueous solution is extracted several times with ether and the combined ether extracts are washed with brine and sodium bicarbonate, dried over magnesium sulfate, filtered and evaporated to give 1,3-dimethyl-2-oxabicyclo[2,2,2]octan-6-one-oxime.

Following the above procedure and using in place of 4-(1-hydroxyethyl)-1-methyl-cyclohexane an equivalent amount of (a) 4-(2-hydroxy-2-butyl)-1-methyl-cyclohexene, there is obtained the intermediate 2-chloro-5-(2-hydroxy-2-butyl)-2-methyl-cyclohexane oxime, which upon dehydrohalogenation in accordance with the above procedure yields (a) 3-ethyl-1,3-dimethyl-2-oxabicyclo[2,2,2]octan-6-one-oxime.

EXAMPLE 2

1,3-Dimethyl-2-oxabicyclo[2,2,2]octan-6-one

To a mixture of 20.5 g. 1,3-dimethyl-2-oxabicyclo[2,2,2]octan-6-one-oxime, 16 g. sodium nitrite, 350 ml. water and 100 ml. diethylether at 25° C. there is added dropwise 100 ml. of 2 N sulfuric acid and the mixture is allowed to stand with occasional stirring for 3 hours. The organic layer is washed with 10% aqueous sodium bicarbonate and evaporated. To the resulting residue at 0° C. there is added 70 ml. concentrated ammonium hydroxide. This mixture is then extracted several times with diethyl ether and the combined ether extracts are dried over magnesium sulfate and evaporated to give 1,3-dimethyl-2-oxabicyclo[2,2,2]octan-6-one.

Following the above procedure and using in place of 1,3-dimethyl-2-oxabicyclo[2,2,2]octan-6-one-oxime an equivalent amount of (a) 3-ethyl-1,3-dimethyl-2-oxabicyclo[2,2,2]octan-6-one-oxime there is obtained (a) 3-ethyl-1,3-dimethyl-2-oxabicyclo[2,2,2]octan-6-one.

EXAMPLE 3

1,3-Dimethyl-2-oxabicyclo[2,2,2]-octan-5,6-dione-5-oxime

To an ice-cooled solution prepared by adding 46 g. (0.3 mole) 1,3-dimethyl-2-oxabicyclo[2,2,2]octan-6-one to a solution of 5 g. of hydrogen chloride gas in 250 ml. diethyl ether is added dropwise 25 ml. of ethylnitrite and after the temperature stabilizes, the mixture is allowed to stand at an ambient temperature for 24 hours, then washed with aqueous sodium bicarbonate solution. After evaporation of the ether, the resulting oil is distilled, hielding 1,3-dimethyl-2-oxabicyclo[2,2,2]octan-5,6-dione-5-oxime; b.p. 130°–140° C./0.01 torr.

Following the above procedure and using in place of 1,3-dimethyl-2-oxabicyclo[2,2,2]octan-6-one an equivalent amount of (a) 3-ethyl-1,3-dimethyl-2-oxabicyclo[2,2,2]octan-6-one there is obtained (a) 3-ethyl-1,3-dimethyl-2-oxabicyclo[2,2,2]octan-5,6-dione-5-oxime.

EXAMPLE 4

1,3-Dimethyl-2-oxabicyclo[2,2,2]octan-5,6-dione-5-oxime-6-hydrazone

A mixture of 1.83 g. (0.01 mole) 1,3-dimethyl-2-oxabicyclo[2,2,2]octan-5,6-dione-5-oxime and 0.35 ml. (0.011 mole) anhydrous hydrazine (98%) in 25 ml. absolute ethanol is refluxed under nitrogen at a bath temperature of 80° C. for 1 hour. Evaporation of the solvent gives 1,3-dimethyl-2-oxa-bicyclo[2,2,2]octan-5,6-dione-5-oxime-6-hydrazone.

Following the above procedure and using in place of 1,3-dimethyl-2-oxabicyclo[2,2,2]octan-5,6-dione-5-oxime an equivalent amount of (a) 3-ethyl-1,3-dimethyl-2-oxabicyclo[2,2,2]octan-5,6-dione-5-oxime there is obtained (a) 3-ethyl-1,3-dimethyl-2-oxabicyclo[2,2,2]octan-5,6-dione-5-oxime-6-hydrazone.

EXAMPLE 5

3-Phenyl-5,8-dihydro-6,8-dimethyl-5,8-ethano-6H-pyrano[4,3-e]-as-triazine-4-oxide A solution of 1.97 g. (0.01 mole) 1,3-dimethyl-2-oxabicyclo[2,2,2]octan-5,6-dione-5-oxime-6-hydrazone in 10 ml. trimethylorthobenzoate is refluxed under nitrogen for 18 hours at a bath temperature of 140° C. during which time all distillate is removed. The resulting mixture is cooled and evaporated to dryness in vacuo. After filtering the residue dissolved in 2% methanol-chloroform through silica gel, and evaporation of the filtrate gives 3-phenyl-5,8-dihydro-6,8-dimethyl-5,8-ethano-6H-pyrano[4,3-e]-as-triazine-4-oxide.

Following the above procedure and using in place of 1,3-dimethyl-2-oxabicyclo[2,2,2]octan-5,6-dione-5-oxime-6-hydrazone an equivalent amount of (a) 3-ethyl-1,3-dimethyl-2-oxabicyclo[2,2,2]octan-5,6-dione-5-oxime-6-hydrazone
there is obtained
  (a)  3-phenyl-5,8-dihydro-6-ethyl-6,8-dimethyl-5,8-ethano-6H-pyrano[4,3-e]-as-triazine-4-oxide.

Again following the above procedure and using in place of trimethylorthobenzoate an equivalent amount of
  (b) p-chloro-trimethylorthobenzoate,
  (c) p-fluoro-trimethylorthobenzoate,
  (d) p-methyl-trimethylorthobenzoate,
  (e) p-methoxy-trimethylorthobenzoate,
  (f) m-trifluoromethyl-trimethylorthobenzoate,
  (g) p-amino-trimethylorthobenzoate,
  (h) p-nitro-trimethylorthobenzoate,
  (i) m-nitro-trimethylorthobenzoate,
  (j) m-chloro-trimethylorthobenzoate, or
  (k) 3,4-dimethoxy-trimethylorthobenzoate,
there is obtained
  (b) 3-(p-chlorophenyl)-5,8-dihydro-6,8-dimethyl-5,8-ethano-6H-pyrano[4,3-e]-as-triazine-4-oxide,
  (c) 3-(p-fluorophenyl)-5,8-dihydro-6,8-dimethyl-5,8-ethano-6H-pyrano[4,3-e]-as-triazine-4-oxide,
  (d) 3-(p-tolyl)-5,8-dihydro-6,8-dimethyl-5,8-ethano-6H-pyrano[4,3-e]-as-triazine-4-oxide,
  (e) 3-(p-anisyl)-5,8-dihydro-6,8-dimethyl-5,8-ethano-6H-pyrano[4,3-e]-as-triazine-4-oxide,
  (f) 3-(m-trifluoromethylphenyl)-5,8-dihydro-6,8-dimethyl-5,8-ethano-6H-pyrano[4,3-e]-as-triazine-4-oxide,
  (g) 3-(p-aminophenyl)-5,8-dihydro-6,8-dimethyl-5,8-ethano-6H-pyrano[4,3-e]-as-triazine-4-oxide,
  (h) 3-(p-nitrophenyl)-5,8-dihydro-6,8-dimethyl-5,8-ethano-6H-pyrano[4,3-e]-as-triazine-4-oxide,
  (i) 3-(m-nitrophenyl)-5,8-dihydro-6,8-dimethyl-5,8-ethano-6H-pyrano[4,3-e]-as-triazine-4-oxide,
  (j) 3-(m-chlorophenyl)-5,8-dihydro-6,8-dimethyl-5,8-ethano-6H-pyrano[4,3-e]-as-triazine-4-oxide, or
  (k) 3-(3,4-dimethoxyphenyl)-5,8-dihydro-6,8-dimethyl-5,8-ethano-6H-pyrano[4,3-e]-as-triazine-4-oxide, respectively.

Also following the above procedure and using in place of 1,3-dimethyl-2-oxabicyclo[2,2,2]octan-5,6-dione-5-oxime-6-hydrazone an equivalent amount of 3-ethyl-1,3-dimethyl-2-oxabicyclo[2,2,2]octan-5,6-dione-5-oxime-6-hydrazone and using in place of trimethylorthobenzoate an equivalent amount of
  (l) m-trifluoromethyl-trimethylorthobenzoate,
  (m) p-nitro-trimethylorthobenzoate, or
  (n) m-nitro-trimethylorthobenzoate, there is obtained
  (l) 3-(m-trifluoromethylphenyl)-5,8-dihydro-6-ethyl-6,8-dimethyl-5,8-ethano-6H-pyrano[4,3-e]-as-triazine-4-oxide,
  (m) 3-(p-nitrophenyl)-5,8-dihydro-6-ethyl-6,8-dimethyl-5,8-ethano-6H-pyrano[4,3-e]-as-triazine-4-oxide, or
  (n) 3-(m-nitrophenyl)-5,8-dihydro-6-ethyl-6,8-dimethyl-5,8-dihydro-6-ethyl-6,8-dimethyl-5,8-ethano-6H-pyrano[4,3-e]-as-triazine-4-oxide, respectively.

The 3-(m-trifluoromethylphenyl)-5,8-dihydro-6,8-dimethyl-5,8-ethano-6H-pyrano[4,3-e]-as-triazine-4-oxide of this example is a particularly effective sleep inducer when orally administered to an animal in need of said treatment at a dosage of 200 mg. just before bedtime.

EXAMPLE 6

3-Phenyl-5,8-dihydro-6,8-dimethyl-5,8-ethano-6H-pyrano[4,3-e]-as-triazine

To a solution of 1.66 g. (0.006 mole) 3-phenyl-5,8-dihydro-6,8-dimethyl-5,8-ethano-6H-pyrano[4,3-e]-as-triazine-4-oxide and 1.50 g. (0.018 mole) cyclohexene in 30 ml. absolute ethanol there is added 60 mg. 10% palladium on charcoal. The resulting mixture is refluxed under a nitrogen atmosphere for 18 hours. The catalyst is then removed by filtration and the filtrate evaporated to give 3-phenyl-5,8-dihydro-6,8-dimethyl-5,8-ethano-6H-pyrano[4,3-e]-as-triazine.

Following the above procedure and using in place of 3-phenyl-5,8-dihydro-6,8-dimethyl-5,8-ethano-6H-pyrano[4,3-e]-as-triazine-4-oxide an equivalent amount of
  (a) 3-phenyl-5,8-dihydro-6-ethyl-6,8-dimethyl-5,8-ethano-6H-pyrano[4,3-e]-as-triazine-4-oxide
there is obtained
  (a) 3-phenyl-5,8-dihydro-6-ethyl-6,8-dimethyl-5,8-ethano-6H-pyrano[4,3-e]-as-triazine.

Following the above procedure and using in place of 3-phenyl-5,8-dihydro-6,8-dimethyl-5,8-ethano-6H-pyrano[4,3-e]-as-triazine-4-oxide an equivalent amount of
  (b) 3-(p-chlorophenyl)-5,8-dihydro-6,8-dimethyl-5,8-ethano-6H-pyrano[4,3-e]-as-triazine-4-oxide,
  (c) 3-(p-fluorophenyl)-5,8-dihydro-6,8-dimethyl-5,8-ethano-6H-pyrano[4,3-e]-as-triazine-4-oxide,
  (d) 3-(p-tolyl)-5,8-dihydro-6,8-dimethyl-5,8-ethano-6H-pyrano[4,3-e]-as-triazine-4-oxide,
  (e) 3-(p-anisyl)-5,8-dihydro-6,8-dimethyl-5,8-ethano-6H-pyrano[4,3-e]-as-triazine-4-oxide,
  (f) 3-(m-trifluoromethylphenyl)-5,8-dihydro-6,8-dimethyl-5,8-ethano-6H-pyrano[4,3-e]-as-triazine-4-oxide,
  (g) 3-(p-aminophenyl)-5,8-dihydro-6,8-dimethyl-5,8-ethano-6H-pyrano[4,3-e]-as-triazine-4-oxide,
  (h) 3-(p-nitrophenyl)-5,8-dihydro-6,8-dimethyl-5,8-ethano-6H-pyrano[4,3-e]-as-triazine-4-oxide,
  (i) 3-(m-nitrophenyl)-5,8-dihydro-6,8-dimethyl-5,8-ethano-6H-pyrano[4,3-e]-as-triazine-4-oxide,
  (j) 3-(m-chlorophenyl)-5,8-dihydro-6,8-dimethyl-5,8-ethano-6H-pyrano[4,3-e]-as-triazine-4oxide, or
  (k) 3-(3,4-dimethoxyphenyl)-5,8-dihydro-6,8-dimethyl-5,8-ethano-6H-pyrano[4,3-e]-as-triazine-4-oxide,
there is obtained
  (b) 3-(p-chlorophenyl)-5,8-dihydro-6,8-dimethyl-5,8-ethano-6H-pyrano[4,3-e]-as-triazine,
  (c) 3-(p-fluorophenyl)-5,8-dihydro-6,8-dimethyl-5,8-ethano-6H-pyrano[4,3-e]-as-triazine,
  (d) 3-(p-tolyl)-5,8-dihydro-6,8-dimethyl-5,8-ethano-6H-pyrano[4,3-e]-as-triazine,
  (e) 3-(p-anisyl)-5,8-dihydro-6,8-dimethyl-5,8-ethano-6H-pyrano[4,3-e]-as-triazine,
  (f) 3-(m-trifluoromethylphenyl)-5,8-dihydro-6,8-dimethyl-5,8-ethano-6H-pyrano[4,3-e]-as-triazine,
  (g) 3-(p-aminophenyl)-5,8-dihydro-6,8-dimethyl-5,8-ethano-6H-pyrano[4,3-e]-as-triazine,
  (h) 3-(p-nitrophenyl)-5,8-dihydro-6,8-dimethyl-5,8-ethano-6H-pyrano[4,3-e]-as-triazine,
  (i) 3-(m-nitrophenyl)-5,8-dihydro-6,8-dimethyl-5,8-ethano-6H-pyrano[4,3-e]-as-triazine,
  (j) 3-(m-chlorophenyl)-5,8-dihydro-6,8-dimethyl-5,8-ethano-6H-pyrano[4,3-e]-as-triazine, or (k) 3-(3,4-dimethoxyphenyl)-5,8-dihydro-6,8-dimethyl-5,8-ethano-6H-pyrano[4,3-e]-as-triazine, respectively.

Again following the above procedure and using in place of 3-phenyl-5,8-dihydro-6,8-dimethyl-5,8-ethano-6H-pyrano[4,3-e]-as-triazine-4-oxide an equivalent amount of (l) 3-(m-trifluoromethylphenyl)-5,8-dihydro-6-ethyl-6,8-dimethyl-5,8-ethano-6H-pyrano[4,3-e]-as-triazine-4-oxide, (m) 3-(p-nitrophenyl)-5,8-dihydro-6-ethyl-6,8-dimethyl-5,8-ethano-6H-pyrano[4,3-e]-as-triazine-4-oxide, or (n) 3-(m-nitrophenyl)-5,8-dihydro-6-ethyl-6,8-dimethyl-5,8-ethano-6H-pyrano[4,3-e]-as-triazine-4-oxide there is obtained (l) 3-(m-trifluoromethylphenyl)-5,8-dihydro-6-ethyl-6,8-dimethyl-5,8-ethano-6H-pyrano[4,3-e]-as-triazine, (m) 3-(p-nitrophenyl)-5,8-dihydro-6-ethyl-6,8-dimethyl-5,8-ethano-6H-pyrano[4,3-e]-as-triazine, or (n) 3-(m-nitrophenyl)-5,8-dihydro-6-ethyl-6,8-dimethyl-5,8-ethano-6H-pyrano[4,3-e]-as-triazine, respectively.

What is claimed is:

1. A compound of the formula

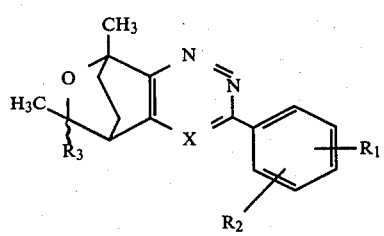

wherein $R_1$ and $R_2$ each independently represent hydrogen, halo having an atomic weight of about 19 to 36, lower alkyl, straight chain lower alkoxy, amino, nitro or trifluoromethyl, and $R_3$ represents hydrogen or lower alkyl, and X represents

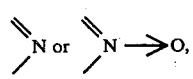

provided that (i) when one of $R_1$ and $R_2$ represents nitro, the other is other than nitro or trifluoromethyl;

(ii) when $R_1$ and $R_2$ represent trifluoromethyl, they are on other than adjacent carbon atoms; and (iii) when $R_1$ and $R_2$ represent t-butyl, they are on other than adjacent carbon atoms, and (iv) when one of $R_1$ and $R_2$ is trifluoromethyl and the other is t-butyl, they are on other than adjacent carbon atoms.

2. A compound of the formula

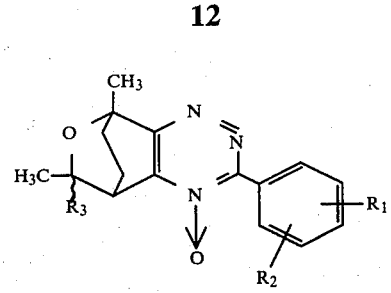

where $R_1$, $R_2$, $R_3$ and the provisos are as defined in claim 1, or a pharmaceutically acceptable salt thereof.

3. A compound of the formula

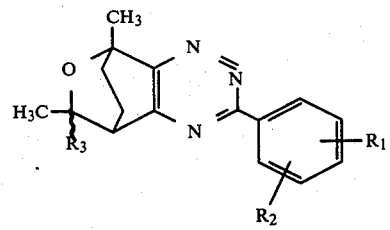

where $R_1$, $R_2$, $R_3$ and the provisos are as defined in claim 1, or a pharmaceutically acceptable salt thereof.

4. A compound of the formula

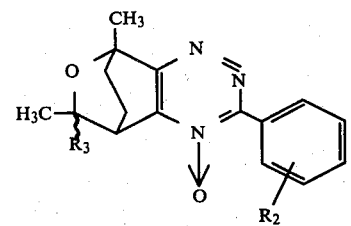

wherein $R_2$, $R_3$ and the provisos are as defined in claim 1, or a pharmaceutically acceptable salt thereof.

5. A compound of the formula

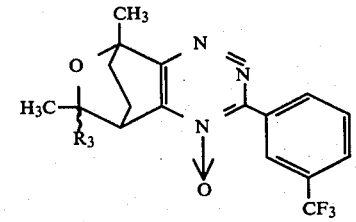

wherein $R_3$ is as defined in claim 1, or a pharmaceutically acceptable salt thereof.

6. A compound of the formula

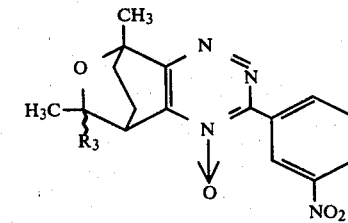

wherein R₃ is as defined in claim 1, or a pharmaceutically acceptable salt thereof.

7. A pharmaceutically acceptable salt of a compound of claim 1.

8. The compound of claim 1 which is 3-phenyl-5,8-dihydro-6,8-dimethyl-5,8-ethano-6H-pyrano[4,3-e]-as-triazine-4-oxide.

9. The compound of claim 1 which is 3-phenyl-5,8-dihydro-6,8-dimethyl-5,8-ethano-6H-pyrano[4,3-e]-as-triazine.

10. The compound of claim 1 which is 3-(m-trifluoromethylphenyl)-5,8-dihydro-6,8-dimethyl-5,8-ethano-6H-pyrano[4,3-e]-as-triazine-4-oxide.

11. The compound of claim 1 which is 3-(m-trifluoromethylphenyl)-5,8-dihydro-6,8-dimethyl-5,8-ethano-6H-pyrano[4,3-e]-as-triazine.

12. The compound of claim 1 which is 3-(m-nitrophenyl)-5,8-dihydro-6,8-dimethyl-5,8-ethano-6H-pyrano[4,3-e]-as-triazine-4-oxide.

13. The compound of claim 1 which is 3-(m-nitrophenyl)-5,8-dihydro-6,8-dimethyl-5,8-ethano-6H-pyrano[4,3-e]-as-triazine.

14. The compound of claim 1 which is 3-(p-fluorophenyl)-5,8-dihydro-6,8-dimethyl-5,8-ethano-6H-pyrano[4,3-e]-as-triazine-4-oxide.

15. The compound of claim 1 which is 3-(p-fluorophenyl)-5,8-dihydro-6,8-dimethyl-5,8-ethano-6H-pyrano[4,3-e]-as-triazine.

16. The compound of claim 1 which is 3-phenyl-5,8-dihydro-6-ethyl-6,8-dimethyl-5,8-ethano-6H-pyrano[4,3-e]-as-triazine.

17. A method of inducing sleep which comprises administering a sleep-inducing effective amount of a compound according to claim 1.

18. A pharmaceutical composition comprising a compound of claim 1 and a pharmaceutically acceptable diluent or carrier therefor.

* * * * *

UNITED STATES PATENT AND TRADEMARK OFFICE
CERTIFICATE OF CORRECTION

PATENT NO. : 4,285,944

DATED : August 25, 1981

INVENTOR(S) : Gregory B. Bennett

It is certified that error appears in the above—identified patent and that said Letters Patent is hereby corrected as shown below:

Column 2, at the top left-hand side of the column; delete the formula

"  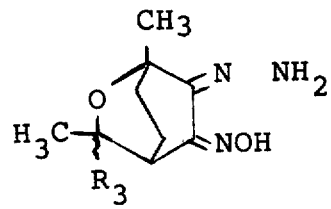  "

and substitute therefor the formula

--  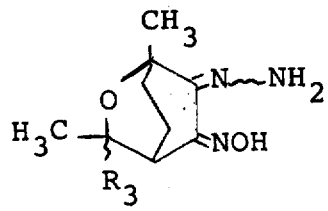  --

UNITED STATES PATENT AND TRADEMARK OFFICE
CERTIFICATE OF CORRECTION

PATENT NO. : 4,285,944  
DATED : August 25, 1981  
INVENTOR(S) : Gregory B. Bennett Page 2 of 2

It is certified that error appears in the above—identified patent and that said Letters Patent is hereby corrected as shown below:

Column 3, to the right directly above line 51; delete the formula

" 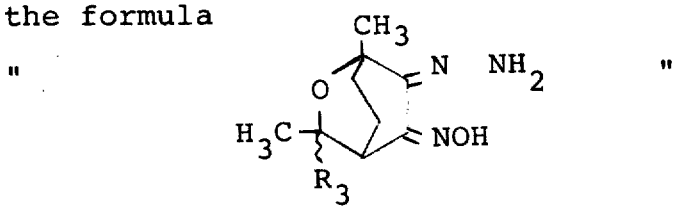 "

and substitute therefor

-- 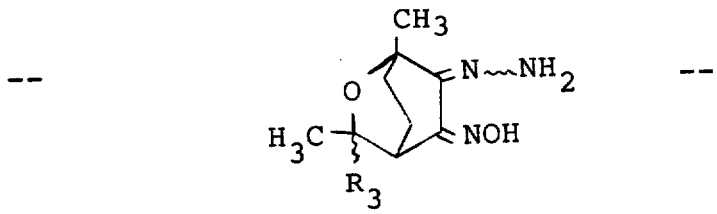 --

Signed and Sealed this

Eighteenth Day of January 1983

[SEAL]

Attest:

Attesting Officer

GERALD J. MOSSINGHOFF  
Commissioner of Patents and Trademarks